United States Patent [19]
Nitzan

[11] Patent Number: 5,897,522
[45] Date of Patent: *Apr. 27, 1999

[54] FLEXIBLE THIN LAYER OPEN ELECTROCHEMICAL CELL AND APPLICATIONS OF SAME

[75] Inventor: Zvi Nitzan, Petah Tikva, Israel

[73] Assignee: Power Paper Ltd., Kibbutz Einat, Israel

[ * ] Notice: This patent is subject to a terminal disclaimer.

[21] Appl. No.: 08/873,868

[22] Filed: Jun. 12, 1997

Related U.S. Application Data

[63] Continuation-in-part of application No. 08/575,190, Dec. 20, 1995, Pat. No. 5,652,043.

[51] Int. Cl.$^6$ .................. A61N 1/30; B32B 9/00
[52] U.S. Cl. .................. 604/20; 428/209; 428/210; 428/688; 428/701; 429/82; 429/127; 429/152; 429/162; 429/224; 429/229
[58] Field of Search .................. 604/20, 21, 890.1; 128/114.1; 602/47, 48, 58; 428/209, 210, 688, 701; 429/82, 127, 152, 162, 224, 229; 607/152

[56] References Cited

U.S. PATENT DOCUMENTS

| | | | |
|---|---|---|---|
| 4,172,015 | 10/1979 | Bamford et al. | 204/1 T |
| 4,552,624 | 11/1985 | Clarkson | 204/1 T |
| 5,603,955 | 2/1997 | Gehrke et al. | 424/484 |
| 5,641,590 | 6/1997 | Sato et al. | 429/192 |
| 5,652,043 | 7/1997 | Nitzan | 428/209 |
| 5,730,716 | 3/1998 | Beck et al. | 604/20 |
| 5,782,893 | 7/1998 | Dennis, III | 607/48 |

*Primary Examiner*—Wynn Wood Coggins
*Assistant Examiner*—Sharon Finkel
*Attorney, Agent, or Firm*—Mark M. Friedman

[57] ABSTRACT

An application comprising an electrically operated device and a flexible thin layer open liquid state electrochemical cell for providing the device with electrical power for its operation, the electrochemical cell including a first layer of insoluble negative pole, a second layer of insoluble positive pole and a third layer of aqueous electrolyte, the third layer being disposed between the first and second layers and including (a) a deliquescent material for keeping the open cell wet at all times; (b) an electroactive soluble material for obtaining required ionic conductivity; and (c) a watersoluble polymer for obtaining a required viscosity for adhering the first and second layers to the third layer.

30 Claims, 5 Drawing Sheets

ND APPLICATIONS OF SAME

FLEXIBLE THIN LAYER OPEN ELECTROCHEMICAL CELL AND APPLICATIONS OF SAME

This is a continuation-in-part of U.S. patent application Ser. No. 08/575,190, filed Dec. 20, 1995, now U.S. Pat. No. 5,652,043, issued Jul. 29, 1997.

FIELD AND BACKGROUND OF THE INVENTION

The present invention relates to electrochemical cells which are used as battery power sources by converting chemical energy to electrical energy. More particularly, the present invention relates to a primary or rechargeable electrochemical cell to be used as a regular or rechargeable battery which accomplishes the conversion of chemical energy to electrical energy using a wet (e.g., liquid state) electrolyte, yet maintain a flexible thin layer and open configuration. The present invention further relates to applications of such cell.

The ever-growing development of miniaturized and portable electrically powered devices of compact design such as for example cellular phones, voice recording and playing devices, watches, motion and still cameras, liquid crystal displays, electronic calculators, IC cards, temperature sensors, hearing aids, pressure sensitive buzzers, etc., generates an ever-growing need of compact thin layer batteries for their operation. Therefore, there is a need for reliable thin layer electrochemical cells to be used as batteries in such devices.

Batteries can be broadly classified into two categories in which the batteries of the first category include wet electrolytes (i.e., liquid state batteries), whereas batteries of the second category include solid state electrolyte. Although solid state batteries have an inherent advantage, they do not dry out and do not leak, they suffer major disadvantages when compared with liquid state batteries since, due to limited diffusion rates of ions through a solid, their operation is temperature dependent to a much larger extent, and many operate well only under elevated temperatures; and, the limited diffusion rates thus described, characterize solid state batteries with low ratio of electrical energy generated vs. their potential chemical energy.

Liquid state thin layer batteries typically include a positive and negative active insoluble material layer put together with a separator interposed therebetween, which separator is soaked with a liquid electrolyte solution, thus functioning as an electrolytic liquid layer. Such batteries, an example of which is disclosed for example in U.S. Pat. No. 4,623,598 to Waki et al., and in Japanese Pat. No. JP 61-55866 to Fuminobu et al., have to be sealed within a sheathing film to prevent liquid evaporation, and are therefore closed electrochemical cells. Being closed cells, these batteries tend to swell upon storage due to evolution of gases which is a fatal problem in thin layer batteries having no mechanical support, the pressure imposed by the accumulated gases leads to layers separation, thus turning the battery inoperative. Means to overcome this problem include (i) the use of a polymer increased viscosity agent, such as hydroxyethylcellulose, applied to adhere (i.e., glue) the battery layers together, thus to overcome the inherent problem of such batteries imposed by lack of solid support; and, (ii) addition of mercury to prevent the formation of gases, especially hydrogen. However, the polymer is limited in its effectiveness and the mercury is environmental hazardous.

A way to solve the above described limitation was disclosed in U.S. Pat. No. 3,901,732 to Kis et al. in which a gas-permeable electrolyte-impermeable polymeric material which allows venting of undesirable gases formed within the battery while preventing any electrolyte loss from the battery is used as a sheathing film to enclose the battery cell.

However, a more direct and efficient approach to avoid undesired gas accumulation in liquid state thin layer batteries would be to provide these batteries as open cells for facilitated release of gases, while at the same time to provide means to avoid liquid evaporation and drying out of the battery. Such a construction would permit the production of thin layer batteries devoid of casings, which batteries will therefore be thinner, more flexible and simpler and therefore cheaper for mass production.

There is thus a widely recognized need for, and it would be highly advantageous to have, a flexible thin layer open electrochemical cell devoid of both accumulation of gases and liquid evaporation limitations.

SUMMARY OF THE INVENTION

According to the present invention there is provided a flexible thin layer open liquid state electrochemical cell which can be used as a primary or rechargeable power supply for various miniaturized and portable electrically powered devices of compact design. There is further provided a method of manufacturing such a cell. The flexible thin layer open electrochemical cell of the present invention includes a wet electrolyte, yet maintains a flexible, thin and open configuration, thus devoid of accumulation of gases upon storage.

According to further features in preferred embodiments of the invention described below, the cell comprising a first layer of insoluble negative pole, a second layer of insoluble positive pole and a third layer of aqueous electrolyte, the third layer being disposed between the first and second layers and including: (a) a deliquescent material for keeping the open cell wet at all times; (b) an electroactive soluble material for obtaining required ionic conductivity; and, (c) a watersoluble polymer for obtaining a required viscosity for adhering the first and second layers to the third layer.

This cell is used is employed in various applications according to the present invention, which applications call for a cheap cell having a flexible and thin configuration.

Thus, according to still further features in the described preferred embodiments provided is an application comprising an electrically operated device and a flexible thin layer open liquid state electrochemical cell for providing the device with electrical power for its operation, the electrochemical cell including a first layer of insoluble negative pole, a second layer of insoluble positive pole and a third layer of aqueous electrolyte, the third layer being disposed between the first and second layers and including (a) a deliquescent material for keeping the open cell wet at all times; (b) an electroactive soluble material for obtaining required ionic conductivity; and (c) a watersoluble polymer for obtaining a required viscosity for adhering the first and second layers to the third layer.

According to still further features in the described preferred embodiments the device includes a substrate material and at least one electronic component attached to the substrate material, the at least one electronic component is for performing a sensible performance.

According to still further features in the described preferred embodiments the substrate is selected from the group consisting of a greeting card, a business card, a package of a food product and a printed matter.

According to still further features in the described preferred embodiments the sensible performance is audial or visual.

According to still further features in the described preferred embodiments the audial performance is selected from the group consisting of a melody, words of a language and telephone dial tones.

According to still further features in the described preferred embodiments the device includes a power switch.

According to still further features in the described preferred embodiments the at least one electronic component is selected from the group consisting of an audio device and a light emitting device.

According to still further features in the described preferred embodiments the audio device includes an audio chip and an echo chamber.

According to still further features in the described preferred embodiments the light emitting device is a low-current led.

According to still further features in the described preferred embodiments the device is a timer.

According to still further features in the described preferred embodiments the timer includes a substrate material and a timer chip attached to the substrate material, the timer chip is presetable for timing a time period and for prompting a sensible performance when the time period has elapsed.

According to still further features in the described preferred embodiments the performance is by an audio or light emitting device.

According to still further features in the described preferred embodiments the sensible performance is audial or visual.

According to still further features in the described preferred embodiments the audial performance is selected from the group consisting of a melody, words of a language and an alarm.

According to still further features in the described preferred embodiments the timer chip is programmable.

According to still further features in the described preferred embodiments the timer chip is resetable.

According to still further features in the described preferred embodiments the audio device includes an audio chip and an echo chamber.

According to still further features in the described preferred embodiments the light emitting device is a low-current led.

According to still further features in the described preferred embodiments the timer is a drug timer.

According to still further features in the described preferred embodiments the device is an active pad for transdermal delivery of a compound.

According to still further features in the described preferred embodiments for the transdermal delivery of the compound the active pad employs a strategy selected from the group consisting of iontophoresis, ultrasound and electroporation.

According to still further features in the described preferred embodiments the compound is selected from the group consisting of a pharmaceutical compound, a cosmetic compound and an anesthetic compound.

According to still further features in the described preferred embodiments the device is a thermometer.

According to still further features in the described preferred embodiments the thermometer includes a thermistor sensor and an electronic chip, the sensor is for sensing a heat magnitude and converting the heat magnitude into electrical parameter of a magnitude corresponding to the heat, the chip is for quantifying the parameter and for translating the parameter into an output of a temperature value.

According to still further features in the described preferred embodiments the thermometer further includes a display for displaying the temperature value.

According to still further features in the described preferred embodiments the device is a glucose sensor.

According to still further features in the described preferred embodiments the glucose sensor includes a needle for rupturing the skin and obtaining a blood sample, a glucose oxidaze based glucose sensor, a potenciostat and an electronic chip for quantifying a glucose level in the blood sample.

According to still further features in the described preferred embodiments the device is a game.

According to still further features in the described preferred embodiments the game includes distributed un-raveled components, the un-raveled components become revealed if current from the cell arrives simultaneously or in a predetermined order to the components, the arrival of current is activated by a player.

According to still further features in the described preferred embodiments provided is a method of making a flexible thin layer open liquid state electrochemical cell comprising the steps of (a) applying a wet color onto inner sides of first and second substrates, the color being current conductor; (b) before drying, applying a positive pole powder on the wet color of the first substrate and a negative pole powder on the wet color of the second substrate; (c) wetting a porous substance with an aqueous solution containing a deliquescent material, an electroactive soluble material and a watersoluble polymer; and (d) attaching the first and second substrates to the porous substance, such that the inner sides faces the substance, so that a three layers cell is formed.

According to still further features in the described preferred embodiments the method further comprising the step of (e) prior to step (d) applying glue onto the inner sides of the substrate or to both sides of the substance, the application of glue is in accordance with a geometrical configuration.

According to still further features in the described preferred embodiments the method further comprising the step of (f) following step (d) cutting the three layers cell according to the geometrical configuration.

According to still further features in the described preferred embodiments the cutting is effected by a laser.

According to still further features in the described preferred embodiments the method further comprising the step of (e) adding a decorative application onto at least one of the substrates.

According to still further features in the described preferred embodiments provided is a method of printing a flexible thin layer open liquid state electrochemical cell comprising the steps of (a) printing a first layer of wet color onto a substrate, the color being current conductive; (b) before drying, spreading over the first layer a layer of positive pole powder; (c) printing over the layer of positive pole powder a layer of an aqueous solution containing fibers, a deliquescent material, an electroactive soluble material and a watersoluble polymer; (d) before drying, spreading over the layer of aqueous solution a layer of negative pole powder; (e) printing over the layer of negative pole powder a second layer of the color.

According to still further features in the described preferred embodiments the method further comprising the step of (f) before step (a), printing a carbon layer on the substrate.

According to still further features in the described preferred embodiments the method further comprising the step of (f) following step (e), printing a carbon layer over the second layer of the color.

The present invention successfully addresses the shortcomings of the presently known configurations by providing a flexible thin layer open electrochemical cell which does not accumulate gases upon storage, yet it is maintained wet and intact by the use of a deliquescent material for keeping it wet at all times and a watersoluble polymer for obtaining the required viscosity for adhering the pole layers to the aqueous electrolyte layer. Further qualities of the cell include having no outer rigid casting therefore it is thin, light and flexible and may be manufactured in any size, shape, color and applied patterns, hence it is suitable for a variety of applications; cost effectiveness; made of environmental and human friendly materials; and, self sticking via an adhesive backing.

BRIEF DESCRIPTION OF THE DRAWINGS

The invention herein described, by way of example only, with reference to the accompanying drawings, wherein.

DESCRIPTION OF THE PREFERRED EMBODIMENTS

The present invention is of a flexible thin layer open electrochemical cell which can be used as a primary or rechargeable power supply for various miniaturized and portable electrical devices of compact design. The flexible thin layer open electrochemical cell of the present invention includes a wet electrolyte, yet maintains a flexible, thin and open configuration, thus devoid of accumulation of gases upon storage. The present invention is further of various devices operable using the flexible thin layer open electrochemical cell.

The principles and operation of a flexible thin layer open electrochemical cell and its applications according to the present invention may be better understood with reference to the drawings and accompanying descriptions.

Figure 1:
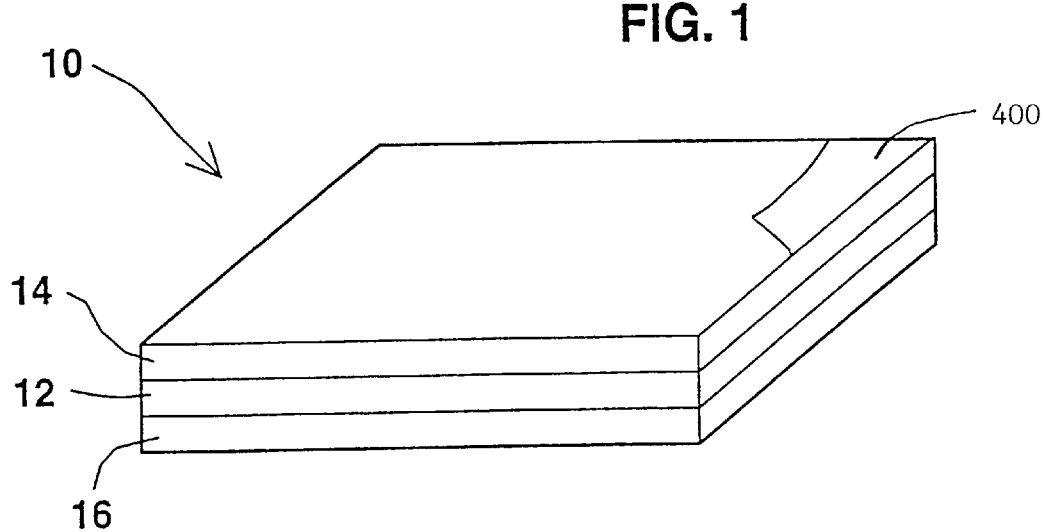
FIG. 1 is a perspective view of a basic configuration of a flexible thin layer open electrochemical cell according to the teachings of the present invention.

Referring now to the drawings, FIG. 1 illustrates a basic configuration of the flexible thin layer open electrochemical cell of the present invention, referred to hereinbelow as cell 10.

Cell 10 includes three layers as follows. A first layer of insoluble negative pole 14, a second layer of insoluble positive pole 16 and a third layer of aqueous electrolyte 12. As used in this document, a discharged negative pole is where an oxidation occurs, whereas the positive pole is where reduction occurs. The aqueous electrolyte layer 12 includes a deliquescent (i.e., hygroscopic) material for keeping open cell 10 wet at all times; an electroactive soluble material for obtaining the required ionic conductivity; and a watersoluble polymer for obtaining the required viscosity for adhering pole layers 14 and 16 to aqueous electrolyte layer 12. Following is a more detailed description of each of layers 14, 16 and 12 and their role in the operation of open cell 10.

Aqueous electrolyte layer 12 typically includes a porous insoluble substance, such as, but not limited to, filter paper, plastic membrane, cellulose membrane, cloth, non-woven material (e.g., cotton fibers), etc., the porous substance is soaked with an aqueous solution including three components: a deliquescent material; an electroactive soluble material; and a watersoluble polymer.

The deliquescent material by being hygroscopic maintains cell 10 moisturized at all times. The level of moisture within open cell 10 may vary depending on deliquescent material selection, its concentration and ambient humidity. Suitable deliquescent materials include, but are not limited to, calcium-chloride, calcium-bromide, potassium-biphosphate, potassium-acetate and combinations thereof.

The electroactive soluble material is selected in accordance with the materials of which the negative and positive pole layers are made. A list of frequently used electroactive soluble materials suitable for the present invention includes, for example, zinc-chloride, zinc-bromide and zinc-fluoride for various primary cells and potassium-hydroxide and sulfuric-acid for rechargeable cells. The watersoluble polymer is employed as an adhesive agent to adhere (i.e., glue) pole layers 14 and 16 to the aqueous electrolyte layer 12. Many types of polymers are suitable ones, such as, for example, polyvinylalcohol, poliacrylamide, polyacrylic acid, polyvinylpyrolidone, polyethylenoxide, agar, agarose, starch, hydroxyethylcellulose and combinations and copolymers thereof.

Each of negative and positive pole layers 14 and 16 includes a mix of a suitable (negative or positive, respectively) active insoluble powder material along with an aqueous solution similar to the solution described hereinabove, which includes a deliquescent material; an electroactive soluble material; and a watersoluble polymer.

It is clear to one having ordinary skills in the art that while the electroactive soluble material should not change, the deliquescent material and the watersoluble polymer may be selected otherwise in the later solution, in other words, the electroactive soluble material should be kept the same in all three layers 12, 14 and 16, whereas the deliquescent material and the watersoluble polymer may vary among the layers, according to the specific application.

Appropriate selection of active insoluble powder materials for the negative 14 and positive 16 pole layers with a matching electroactive soluble material, as exemplified hereinbelow in the Examples section, provides a flexible thin layer cell which can be used as a power supply (i.e., a battery), which cell is open and therefore does not accumulate gases upon storage, yet the hygroscopicality of the deliquescent material ensures that the cell is kept wet at all times although open. Suitable pairs of materials to be used in negative 14 and positive 16 poles include, but are not limited to, manganese-dioxide/zinc; silver-oxide/zinc; cadmium/nickel-oxide; and iron/nickel-oxide (the manganese-dioxide and the silver-oxide are optionally mixed with a conductive carbon powder, as known in the art).

It is clear to one having ordinary skills in the art that a single material may function both as a deliquescent material and as the electroactive soluble material. Such a material should however acquire suitable electroactive and hygroscopic characteristics. Suitable materials of this type include, but are not limited to, zinc-chloride and zinc-bromide.

It is further clear to one having ordinary skills in the art that a single material may function as a deliquescent material and as a watersoluble polymer. Such a material should however acquire suitable hygroscopic and adhesivness characteristics. Suitable materials of this type include, but are not limited to, dextrane, dextranesulfate and combinations and copolymers thereof.

The three layers 12, 14 and 16, presented in FIG. 1 and described hereinabove may be manufactured thin and are flexible, therefore cell 10 is flexible and as thin as 0.3 or less to 1.5 mm. It is presently preferred and will be further detailed below that cell 10 will be manufactured by a suitable printing technology. Suitable printing technologies include, but are not limited to, silk print, offset print, jet printing, lamination, materials evaporation and powder dispersion.

Figure 2:
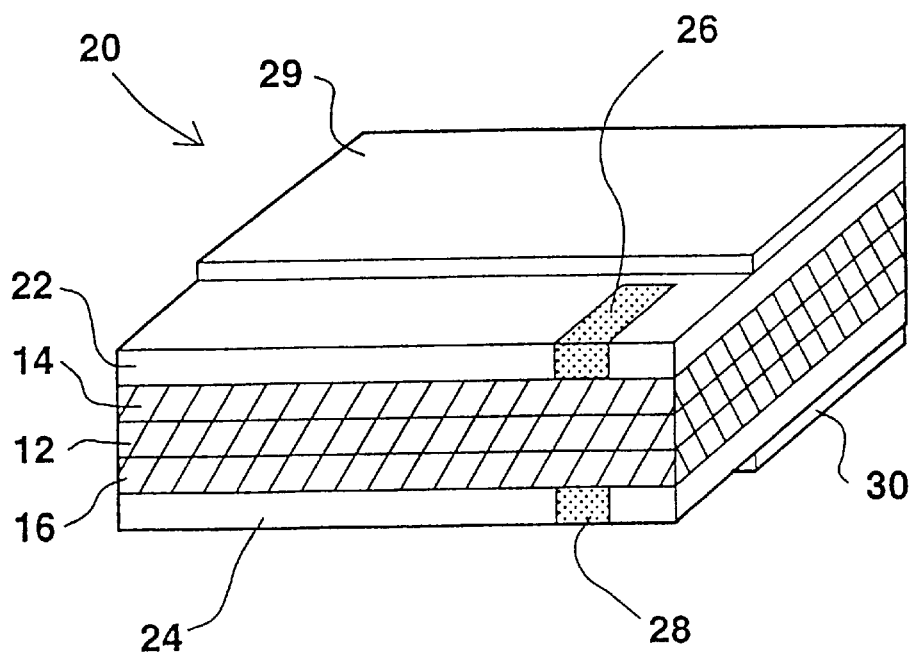
FIG. 2 is a is a perspective view of another possible configuration of a flexible thin layer open electrochemical cell.

Another possible configuration is shown in FIG. 2 illustrating a cell, generally assigned 20. As cell 10, cell 20 also includes layers 12, 14 and 16 (stripped region) forming a basic cell. Cell 20 further includes additional one or two conductive layers 22 and 24, to improve the electronic conductivity of negative 14 and/or positive 16 pole layers. Suitable conductive layers are graphite paper, carbon cloth, etc. Cell 20 also includes negative 26 and positive 28 terminals, which terminals 26 and 28 are in electrical contact with either the corresponding pole layer 14 and 16, respectively, or with the corresponding conductive layer 22 and 24, respectively, or both. Terminals 26 and 28 are made of any suitable materials such as, but not limited to, graphite or metals such as iron, nickel, titanium, copper, stainless steel and mixtures thereof, and are preferably applied to cell 20 by a suitable printing technology such as those listed above.

Terminals 26 and 28 are used to electrically connect cell 20 to a load such as an electrical device. Terminals 26 and 28 may be located in any desired location of cell 20, may acquire any suitable shape and size and, depending on the specific application, terminals 26 and 28 may protrude from the surface and dimensions of cell 20. Cell 20 may further include at least one externally located adhesive backing 29, to enable attaching cell 20 to various surfaces, and/or at least one externally located lamina protective layer 30 to physically protect all other layers.

Figure 3A:
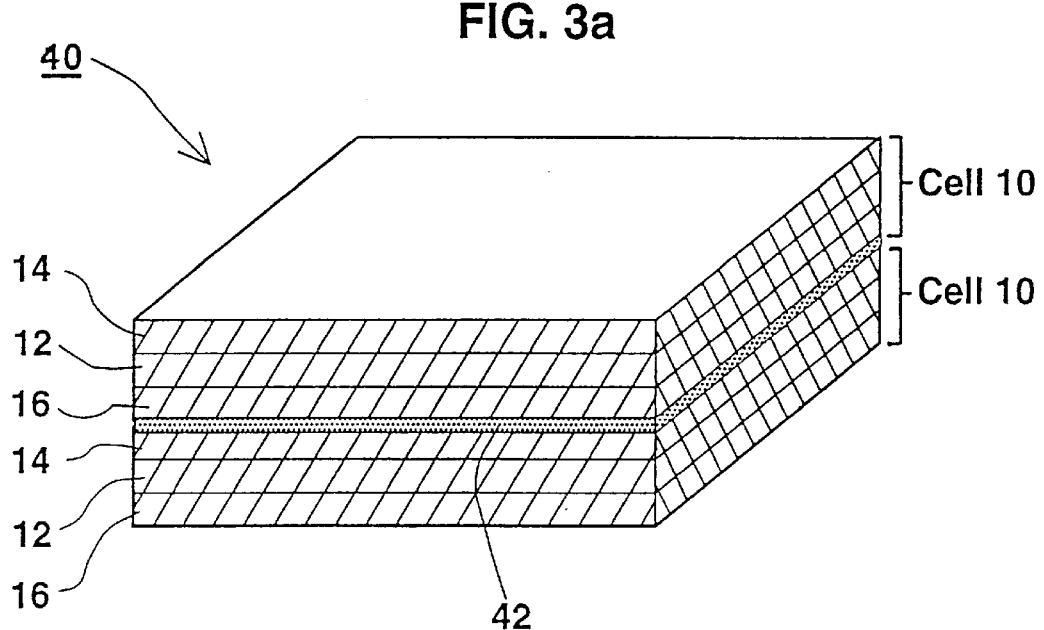
FIGS. 3a and 3b are perspective views of two possible configurations of power supplies formed by a a bi-polar connection of two cells of FIG. 1 and FIG. 2, respectively, to additively increase the electrical energy obtained of thus formed electrical power supplies.
Figure 3B:
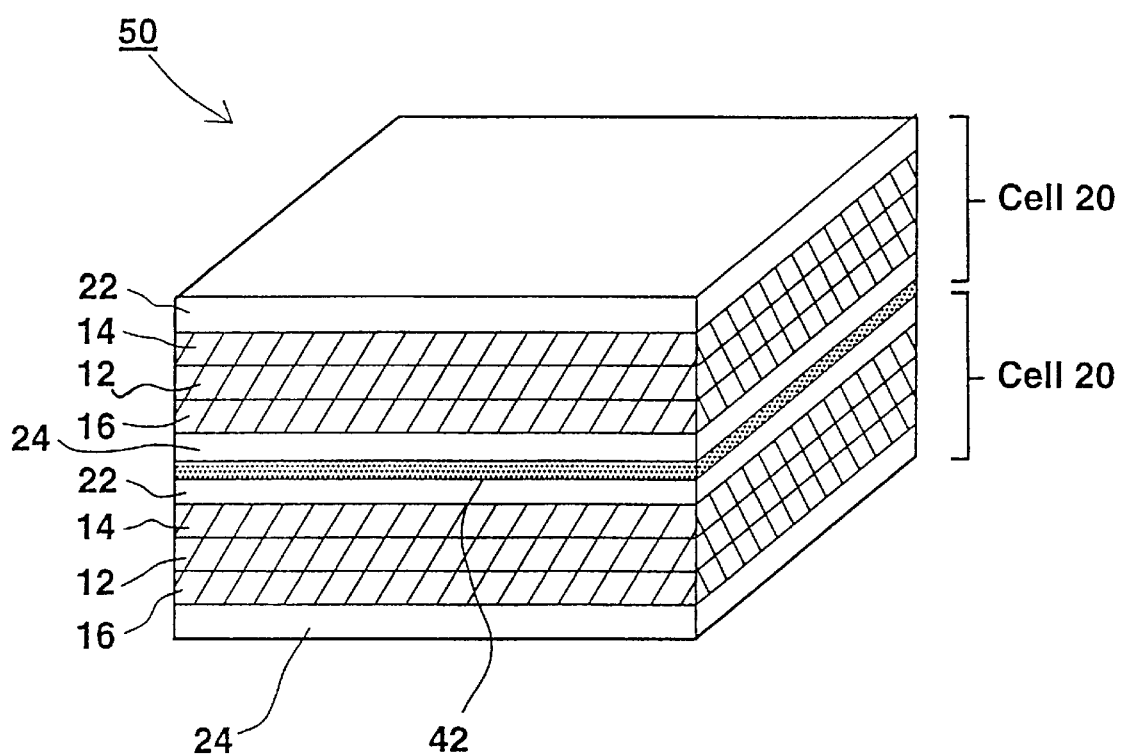

Yet another configuration is shown in FIGS. 3*a*–*b*. Two or more cells 10, as shown in FIG. 3*a*, or cells 20, as shown in FIG. 3*b*, may be electrically connected by a bi-polar connection to additively increase the electrical energy obtained of thus formed electrical power supplies 40 and 50, respectively. For this purpose two or more cells are adhered to one another in a head to tail orientation, as indicated in FIGS. 3*a*–*b* by layers 22, 14, 12, 16 and 24 arrangement, by a conductive double sided adhesive tape, or a conductive glue layer 42 applied for example by a suitable printing technology, and enabling passage of electrons between adjacent cells.

It is clear that electrical power supplies 40 and/or 50 may further include externally located adhesive backing(s) similar to surface 29 shown in FIG. 2 and/or externally located lamina protective layer(s), similar to layer 30 shown in FIG. 2. It is further clear that electrical power supplies 40 and 50 may include a negative and a positive terminal similar to terminals 26 and 28, respectively, of FIG. 2.

The present invention further includes a method of making a flexible thin layer open liquid state electrochemical cells similar to the cells described above, the method includes the steps of (a) wetting a porous substance with an aqueous solution containing a deliquescent material, an electroactive soluble material and a watersoluble polymer; wetting may be achieved by either dipping or printing technologies; (b) applying onto one side of the porous substance a negative pole layer; and, (c) applying onto the second side of the porous substance a positive pole layer. The negative and positive pole layers include active insoluble powder substances mixed with the deliquescent material, electroactive soluble material and watersoluble polymer preferably of the same types as under (a), and are preferably applied using a suitable printing technology selected for example from those listed above.

The method may further include adding to the cell additional layers and parts, such as but not limited to, externally located adhesive backing(s) and/or lamina protective layer (s), and negative and a positive terminals.

Yet, the method may further include bi-polar joining of two or more cells, for example with a conductive double sided adhesive tape or a conductive glue layer applied for example by a suitable printing technology, to form a power supply with an increased power (e.g., substantially doubled, tripled, etc.). According to the present invention such bi-polar joining may be performed by joining together in a head to tail orientation two or more premanufactured cells, or alternatively, directly manufacturing two or more cells thus oriented, by applying suitable layer one after the other, preferably using a suitable printing technology as described above.

The flexible thin layer open electrochemical cell of the present invention has a major advantage over prior art thin layer cells. Since it is an open cell it does not accumulate gases upon storage, yet it is maintained wet and intact by the use of a deliquescent material for keeping it wet at all times and a watersoluble polymer for obtaining the required viscosity for adhering the pole layers to the aqueous electrolyte layer.

The flexible thin layer open electrochemical cell of the present invention has other qualities as follows. First, it has no outer rigid casting therefore it is thin light and flexible and may be manufactured in any size, shape, color and applied patterns, hence it is suitable for a variety of applications. Second, by using a suitable printing technology for its manufacturing its cost is reduced and therefore it may be disposed after use partly since large sheets can be produced and cut to any desired size following printing and partly since this technology is inherently cost effective. Third, it is preferably made of environmental and human friendly materials (it preferably contains no mercury or heavy metals). And finally, it may be manufactured self sticking via an adhesive backing.

Reference in now made to the following examples, which together with the above descriptions, illustrate the invention.

EXAMPLE 1

A solution containing 120 mg of polyvinylalcohol (an aqueous soluble polymer) and 1680 mg of zinc-chloride (a deliquescent material and an electroactive soluble material) in 1.2 ml of water was prepared. This solution had a glue like viscous appearance. A 4.5 cm×7 cm strip of a filter paper was thoroughly wetted with this solution by a printing or dipping technologies. A mixture of 300 mg zinc powder with the above solution was prepared and was printed on one side of the paper strip serving as the negative pole layer. On the other side printed was a mixture of 250 mg manganese-dioxide and 50 mg of a conductive carbon powder, together with the above solution, serving as the positive pole layer. When electrical contacts were made with both sides and were connected over a load an electrical current was measured. A current of 12 microampers per $cm^2$ at a voltage of 1.7÷1.2 volts was easily maintained for five days continuously under room conditions.

EXAMPLE 2

Figure 4:
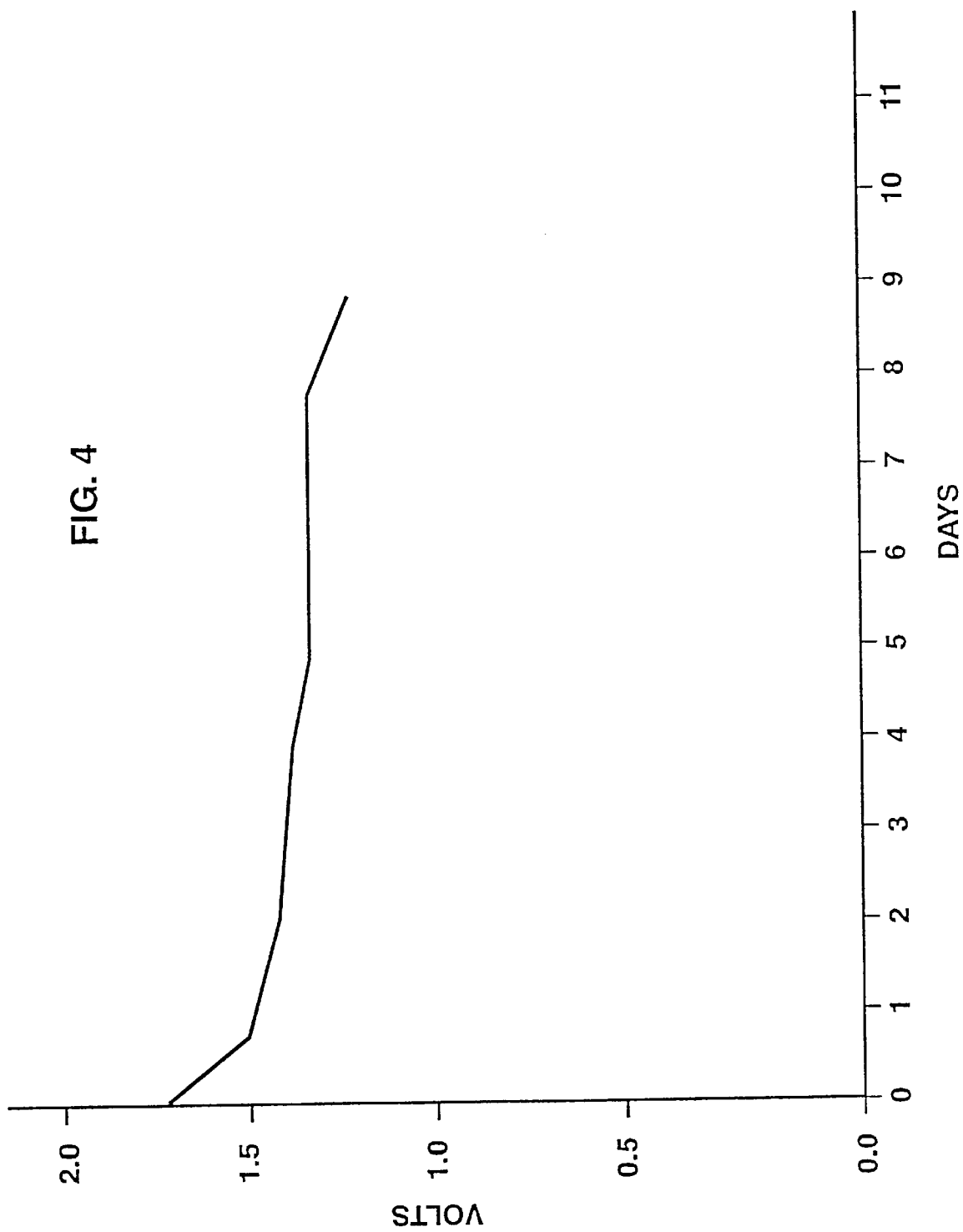
FIG. 4 is a graph presenting the voltage of a flexible thin layer open electrochemical cell according to the present invention, as measured by a voltmeter, as function of time, under room conditions.

An open cell was prepared as described under Example 1 above and was connected to a voltmeter. As shown in FIG. 4, measurement of the voltage produced by the cell under room conditions revealed a pronounced voltage of 1.7÷1.2 sustained for nine successive days.

EXAMPLE 3

A saturated potassium-hydroxide solution is prepared and brought to the viscosity of a glue by mixing with a water soluble polymer. A porous substance (e.g., a filter paper) is thoroughly wetted with this solution and a mixture of the solution with nickel-oxide powder is pasted on one side of the porous substance to form a positive pole layer and, a similar mixture with cadmium powder is pasted on the other side of the porous substance to form a negative pole layer. By connecting a voltmeter to the two sides a voltage of 1.2 volts is measured and a high current is measured when the two layers are contacted over a load. The cell does not dry out in the open and can be recharged if so desired.

EXAMPLE 4

The same potassium-hydroxide solution as in Example 3 is prepared and a porous substance is wetted with it. A mixture of the solution with zinc powder is pasted on one side of the porous substance to form a negative pole layer and a similar mixture with silver-oxide powder containing some carbon powder if so desired is pasted on the other side of the porous substance to form a positive pole layer. By connecting a voltmeter to the two sides a voltage of 1.2 volts is measured and appreciable current is measured when the two layers are contacted over a load. The cell does not dry out in the open and can be recharged if so desired.

EXAMPLE 5

The same potassium-hydroxide solution as in Example 3 is prepared and a porous substance is wetted with it. A mixture of the solution with zinc powder is pasted on one side of the porous substance to form a negative pole layer and a similar mixture with manganese-dioxide powder containing some carbon powder if so desired is pasted on the other side of the porous substance to form a positive pole layer. By connecting a voltmeter to the two sides a voltage of 1.5 volts is measured and appreciable current is measured when the two layers are contacted over a load. The cell does not dry out in the open. Recharging thus formed cell may be troublesome.

EXAMPLE 6

The same potassium-hydroxide solution as in Example 3 is prepared and a porous substance is wetted with it. A mixture of the solution with nickel-oxide powder is pasted on one side of the porous substance to form a positive pole layer and a similar mixture with iron powder is pasted on the other side of the porous substance to form a negative pole layer. By connecting a voltmeter to the two sides a voltage of 0.9 volts is measured and a current can be measured when the two layers are contacted over a load. The cell does not dry out in the open and some recharged is possible if so desired.

EXAMPLE 7

A 30% sulfuric acid solution is prepared and brought to the viscosity of a glue by mixing with a water soluble polymer. A porous substance (e.g., a filter paper) is thoroughly wetted with this solution and a mixture of the solution with lead-oxide is pasted on both sides of the porous substance. Both sides are connected to a power supply and a voltage higher than 2 volts is applied by which the cell is charged. Charge and discharge cycles can be repeated without the cell drying out in the open.

The following Example concerns applications using the open cell as described above as a power source.

EXAMPLE 8

The cell hereinabove described and exemplified may be used in various applications taking advantage of its thinness, lightness flexibility a low manufacturing costs. These qualities render the cell a highly suitable power source for the operation of disposable devices and devices which should maintain a certain flexibility in order to operate well.

In general, any application according to the present invention includes an electrically operated device and a flexible thin layer open liquid state electrochemical cell as hereinabove described. The cell serves for providing the device with electrical power for its operation.

Figure 5:
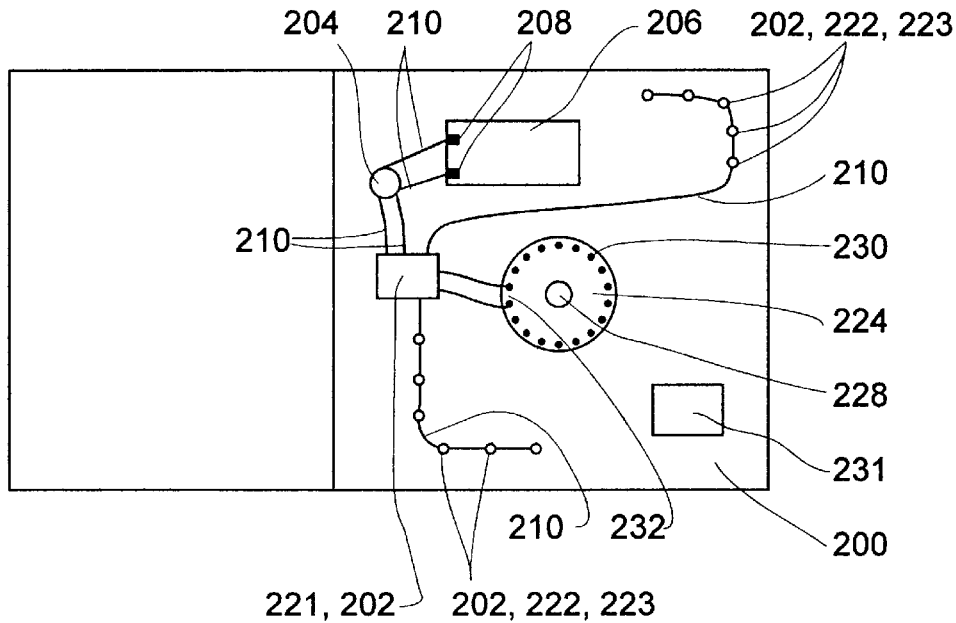
FIG. 5 is schematic depiction of a device which includes a substrate material and at least one electronic component for performing a sensible performance, according to the present invention.

With reference now to FIG. 5. In one application the device includes a substrate material such as paper, carton or plastic board 200 and at least one electronic component 202. Electronic component(s) 202 is attached to substrate material 200 either by adhering or by directly printing electronic component(s) 202 or parts thereof onto substrate 202.

Electronic component 202 is for performing a sensible performance, which is defined herein as a performance which may be sensed by one of the senses. Substrate material 200 may take any suitable shape and be used as, for example, a greeting card, a business card, a package of a food product or any type of printed matter, such as, but not limited to, a magazine, a notebook, a diary, etc.

The sensible performance may thus be used to deliver a message or any type of information to the user or may serve a pleasure in the form of, for example, a melody or a lighting pattern.

Thus, in a preferred embodiment of the invention the sensible performance is audial and/or visual. The audial performance may be of any type and may therefore include a melody, words of a language and/or telephone dial tones. The visual performance may, for example, be of light, of a moving object or of change in color due to the effect of an electrical field/flow of current as for example described in U.S. Pat No. 4,779,962, which is incorporated by reference as if fully set forth herein.

Displayed telephone dial tones may be used in combination with a dual tone multi frequency (DTMF) device attached to a telephone set to dial the toned telephone number, as well known in the art of telephonia.

Electronic component 202 is preferably printed onto substrate material 200, as well as open cell 206, its terminals 208 and the required circuit connections 210. Methods of printing electronic components are well known in the art. One example is U.S. Pat. Nos. 4,353,954 and 4,562,119, both are incorporated by reference as if fully set forth herein. Methods of printing the open cell according to the present invention onto a substrate are described hereinbelow.

In a preferred embodiment of the invention the device includes a power switch 204. Switch 204 is used to operate the device and to stop its operation, if so required.

Figure 6:
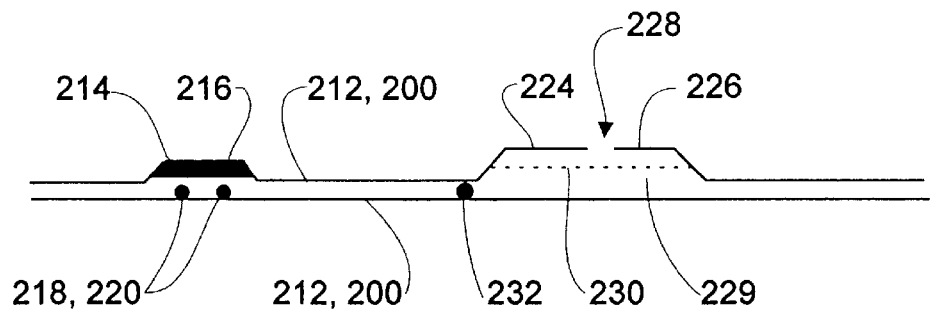
FIG. 6 is schematic cross section of a switch and an echo chamber implemented in the device of FIG. 5.

As shown in FIG. 6, in a preferred embodiment of the invention, switch 204 is formed within two layers 212 of material 200, wherein one of the layers is formed with an elevation 214 covered from the inside with a conductive material, e.g., a layer of conductive carbon, which is positioned above terminals 218, such that pressing elevation 214 results in closing an electrical circuit.

As further shown in FIG. 5, in a preferred embodiment of the invention electronic component 202 is an audio device 220 which includes an audio (voice) chip 221 (e.g., the voice chip "CHIP ON BOARD" distributed by CoMedia Ltd. Hong Kong, Cat. # A53915) and preferably an echo chamber 224 (e.g., the echo chamber "piezoelectric sounder/speaker" distributed by muRata, Holbeinstrasse 21-23 D 8500 Nurenberg 70, Germany) and/or a light emitting device 222. In a preferred embodiment light emitting device 222 is a low-current led 223. Voice chip 221 may record sounds and display the recorded sounds upon command.

As further shown in FIG. 6, in a preferred embodiment of the invention, chamber 224 is formed, similar to switch 204, within layers 212, wherein one of the layers is formed with an elevation 226 and with an opening 228. Within the void 229 thus formed positioned is a vibrating membrane 230, which is connected to a piezoelectric component 232, which vibrates according to instructions received from audio chip 221 (shown in FIG. 5). The combination of membrane 230 and component 232 is known in the art as a piazoceramic plate.

Figure 7:
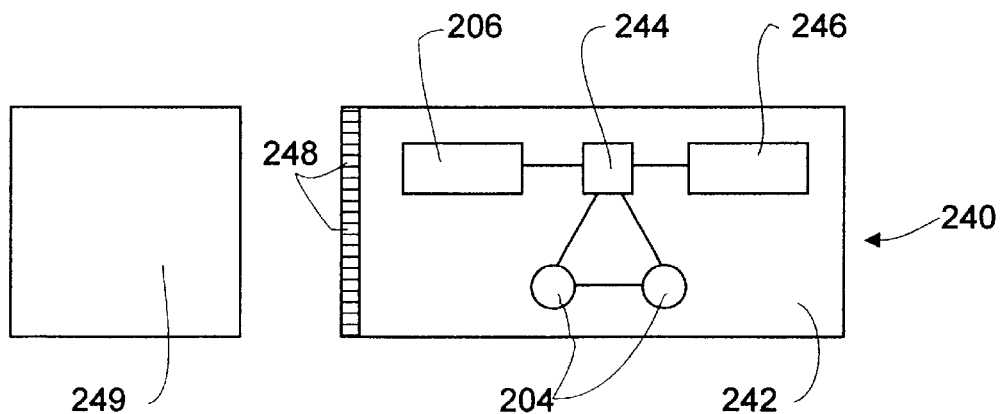
FIG. 7 is schematic depiction of a timer according to the present invention.

With reference to FIG. 7, according to another embodiment of the invention the device is a timer 240. Preferably, timer 240 includes a substrate 242 onto which an open cell 206 according to the present invention is attached, either adhered or printed. Timer 240 further includes a timer chip 244 which can be reset for timing a time period and for prompting a sensible performance when the time period has elapsed. A suitable timer chip is distributed by National Semiconductor Corp., Calif., Cat. # COP888.

As before, the sensible performance is preferably enacted by an audio and/or light emitting device 246, such that the sensible performance is audial (e.g., a melody, words of a language or an alarm) and/or visual.

In a preferred embodiment of the invention timer chip 244 is programmable, i.e., the time period elapses between resetting and prompting the sensible performance is programmable.

Programming is preferably performed by an external programming device 249 (e.g., a computer) which can be connected via suitable connections 248 formed in timer 240 to chip 244. One having ordinary skills in the art would know how to select the required connections between programming device and device 240, so as to enable programming as hereinabove described.

In a preferred embodiment the timer serves as a drug timer, i.e., it indicates that time to take a drug has arrived. In this case substrate 242 is preferably formed as a sticker which may be adhered to a drug container. In this case, the pharmacist would program chip 244 as required for a specific drug via programming device 249 and would adhere timer 240 to the drug container.

In this case, programming device preferably further includes a printer for printing various details such as the drug, the date, the name of the patient and the schedule according to which the drug is to be taken.

Preferably drug timer 240 includes two reset switches 204, which reset timer 240 only when pressed simultaneously, as to avoid accidental reset.

Another use for the open cell according to the present invention is in the active transdermal delivery of compounds such as pharmaceutical, cosmetic and anesthetic compounds.

Figure 8:
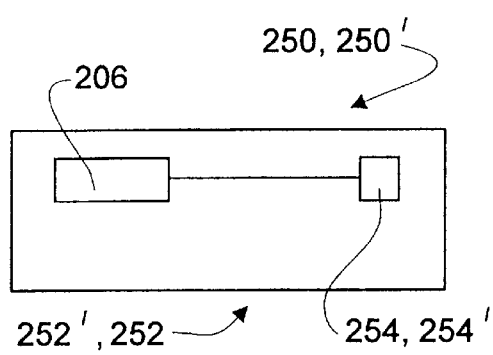
FIG. 8 is schematic depiction of an active pad for transdermal delivery of a compound according to the present invention.

FIG. 8 presents an active pad or patch 250 for transdermal delivery of a compound. Pad 250 has one side 252 which may adhere to the skin of a user. Pad 250 includes the compound which is to be transdermally delivered.

Active transdermal delivery of compounds into the body is well known in the art. Few strategies are employed for transdermal active drug delivery.

Iontophoresis, is employed to deliver small charged molecules across the skin. In this case the compound molecules follow a path dictated by their self charge and the charge imposed on the pad by a power source.

Electroporation employs short and strong pulses of electricity to create temporary openings in the skin through which large molecules can pass. Ultrasound employs high-pitched sound to temporarily disrupt the skin's structure, creating microscopic holes through which large molecules can pass.

According to the strategy employed pad 250 is equipped with the required electronics and/or an ultrasound generator 254.

Further details concerning the functionality and precise construction of active pads are well known in the art and require no further description. Such details are found, for example, in "Breaking the skin barrier", by Ingrid Wickelgren, Popular Science, December 1996, pp. 86–89, "Controlled drug delivery fundamentals and applications". Second edition, J. R. Robinson and V. H. L. Lee editors, Marceldekker Inc. New York, 1987, and U.S. Pat. Nos. 5,169,384; 4,763,660; 5,443,441 and 3,447,537, all are incorporated by reference as if fully set forth herein.

The open cell described above has advantages in use for transdermal drug delivery pads due to its thinness, flexibility and light weigh.

Therefore, according to the present invention pad 250 is supplemented with such a cell 206, which serve as a power source for generating the iontophoresis, ultrasound or electroporation effects, which are required for active transdermal drug delivery.

FIG. 8 will now be used to present an active pad or patch 250' for transdermal recovery of a compound from the body.

Like pad 250, pad 250' has one side 252' which may adhere to the skin of a user. Pad 250' is directed at adsorbing the compound from the body.

Active transdermal recovery of compounds from the body is well known in the art and may employ reverse iontophoresis, reverse electroporation and reverse ultrasound.

According to the strategy employed pad 250' is equipped with the required electronics and/or an ultrasound generator 254'.

Further details concerning the functionality and precise construction of active recovery pads are well known in the art and require no further description. Prior art active recovery pads are manufactured by Signus Inc. California, U.S.A.

The open cell described above has advantages in use for transdermal recovery pads due to its flexibility and light weigh.

Therefore, according to the present invention pad 250' is supplemented with such a cell 206, which serve as a power source for generating the iontophoresis, ultrasound or electroporation effects, which are required for active transdermal recovery.

Figure 9:
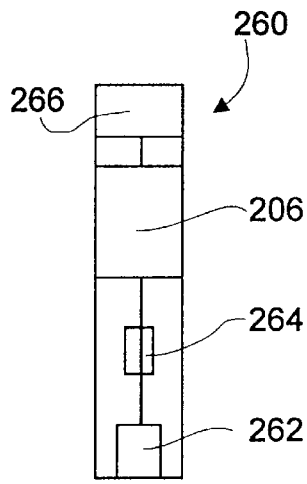
FIG. 9 is schematic depiction of a thermometer according to the present invention.
Figure 10:
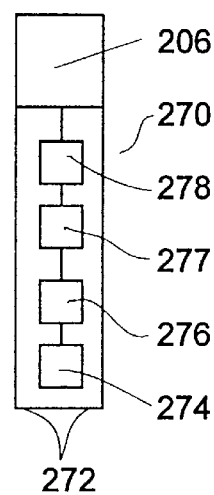
FIG. 10 is schematic depiction of a glucose sensor according to the present invention.

Another use for the open cell according to the present invention is in temperature determinations. Shown in FIG. 9 is an electric thermometer 260 which employs the open cell according to the invention as a power source 206 for a thermistor sensor 262 which serves for sensing a heat magnitude and converting it into an electrical parameter (e.g., resistance, voltage, etc.) of a magnitude corresponding to the heat. A suitable thermistor is distributed by Beta Therm Cat. # 1K7A1. Thermometer 260 further includes an electronic chip 264 for quantifying the electrical parameter and for translating it into an output of a temperature value.

Thermometer 260 further includes a display 266 for displaying the temperature value. Display 260 may include a set of small leds arranged along a temperature scale, such that when a specific led operates, the user can read the temperature from the scale.

Another use for the open cell according to the present invention is in glucose level determinations.

Diabetes is a chronic life-threatening disease which affects over 100 million worldwide. The disease is characterized by the body's inability to properly control its glucose metabolism, most often because of inadequate secretion of the hormone insulin by the pancreas. In normal individuals, when blood glucose begins to rise, a continuous physiological feedback mechanism instructs the pancreas to secrete the appropriate amount of insulin and thereby bring the glucose level down. Diabetics lack this capability and, if untreated, suffer from an uncontrolled blood sugar level with consequent metabolic and circulatory problems that are often crippling of fatal.

In insulin-dependent diabetes, the body's lack of natural insulin is compensated by injections, usually administered several times daily. Insulin dosage, however, must be carefully controlled and excessive insulin will lead to hypoglycemia, low blood glucose, which can cause seizures, brain damage and death. Therefor, most patients receiving insulin therapy must also monitor their blood glucose level, in order to properly regulate the balance their sugar intake and insulin dosage.

The preferred and most common method of ambulatory blood glucose monitoring today is by blood test. Portable blood testing devices include three elements: a needle, enzymatic biosensing material, and an electric reader (optical or resistance). The patient pricks his/her finger with the needle and draws a drop of blood onto a test strip. A biosensing material impregnated on the strip changes color or produces electrochemical current in proportion to the concentration of glucose in the sample. These kits are widely available, including digital-readout meters.

Shown in FIG. 9 is a glucose sensor 270. Sensor 270 includes a needle 272 for rupturing the skin (e.g., the finger skin) of the user and obtaining a blood sample thereof. Needle 272 is preferably a platinum needle. Sensor 270 further includes a glucose oxidaze based glucose sensor 274, a potenciostat 276 and an electronic chip 277 for quantifying the glucose level in the blood sample. Sensor 270 further includes a display 278 for presenting the level of glucose measured in the blood sample in conventional units of concentration (e.g., mg/dl).

The operation of each of the components mentioned in glucose level determinations is well know in the art. Prior art glucose sensors are distributed by, for example, LifeScan Inc. and MediSense Inc. U.S.A.

According to the present invention, as a power source for the operation of glucose sensor 270 serves the inventive open cell 206.

Figure 11:
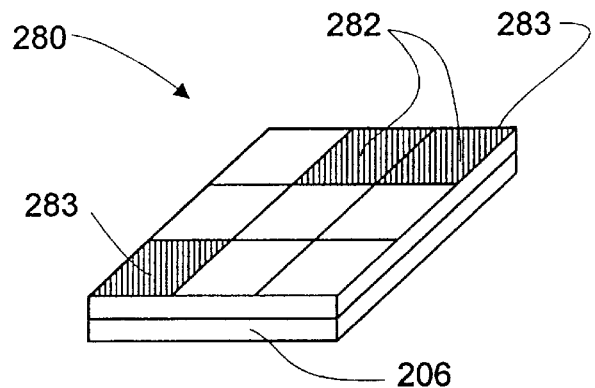
FIG. 11 is schematic depiction of a game according to the present invention.

Another use for the open cell according to the present invention is in games. Shown in FIG. 11 is a game 280 which includes distributed un-raveled components 282 arranged on a substrate 283. Un-raveled components 282 become revealed if current from an open cell 206, as hereinabove described, arrives simultaneously or in a predetermined order to components 282. The arrival of current is activated by a player. To this end components 282 which are to be revealed include a hidden switch, such that when the player presses the component with its finger, the switch closes an electrical circuit.

The game may further include a winning effect(s) which may be any sensible performance, either audial or visual. One of ordinary skills in the art would know how construct components 282 and to generate the winning effect(s).

The production costs of an open cell a described herein are very low since, as further detailed below, the open cell may be mass produced using printing technologies, and further since it requires no casing. The cell may be attached to any device by adhering it to the device or by printing it on the device. Devices which employ the cell are therefore relatively cheap to manufacture and may therefore be disposable. This, in turn, has advantages in many aspects, especially when the device is used for medical purposes such as blood analysis, in mouth temperature determination and transdermal drug delivery or compounds recovery. In the latter, the flexibility of the cell is also a crucial factor since active pads should adhere to the skin at various locations of the body. Since the cell according to the present invention is thin and may cover any surface it is useful in advertising as a part of a medium to deliver information, a game or any other "give away" product which requires power for its operation. To this effect it will be appreciated that the cell may be fabricated from inexpensive, readily available and environmental friendly materials.

The following Example concern methods for manufacturing the thin layer flexible open cell according to the present invention.

EXAMPLE 9

According to the present invention provided is a method of making a flexible thin layer open liquid state electrochemical cell. The method includes the following steps. First a wet color is applied onto inner sides of first and second substrates. Suitable substrates include, but are not limited to, paper, polyester or polypropylene foils. The color is a current conductor. Suitable current conductor colors are distributed under the name "ELECTRODYE" by Acheson Colloiden B. V., the Netherlands, Cat. # 423SS and 109B. Second, before the color dries, a positive pole powder is applied on the wet color of the first substrate and a negative pole powder is applied on the wet color of the second substrate. Since the color is wet, the powders stick to the color and since the color is a current conductor the particles of the respective powders are in electrical contact. Powder application may be devised such that a single layer of powder particles is formed. The cell thus produced will therefore enjoy extra thinness. Third, a porous substance is wetted with an aqueous solution containing a deliquescent material, an electroactive soluble material and a watersoluble polymer. Fourth, the first and second substrates are attached to the porous substance, such that their inner sides face the substance, so that a three layers cell is formed.

In a preferred embodiment of the invention the method further includes the following steps. Fifth, glue is applied onto the inner sides of the substrates or to both sides of the substance. The application of glue is preferably in accordance with a geometrical configuration, such as a star, a circle, a flower shape, etc. Sixth, the three layers cell is cut (e.g., by a laser) according to the geometrical configuration. The glue which is located at the edges of the geometrical configuration ensures that the layers will not separate over time and handling.

In a preferred embodiment of the method, a decorative application is applied onto at least one of the substrates.

Further according to the present invention provided is a method of printing a flexible thin layer open liquid state electrochemical cell. The method includes the following steps. First, a first layer of wet color is printed onto a substrate. The color is a current conductive color. Second, before drying, a layer of a positive pole powder is spread over the first layer of wet color. Third, a layer of an aqueous solution containing fibers, a deliquescent material, an electroactive soluble material and a watersoluble polymer is printed over the layer of positive pole powder. The fibers may be of any type. Suitable fibers include, for example, cotton non-woven fibers. The fibers and their concentration are selected such that upon drying they will form a porous substance. Fourth, before drying, a layer of negative pole powder is spread over the layer of aqueous solution. Fifth, a second layer of the color is printed over the layer of negative pole powder. The result is a three layers battery, substantially as depicted in FIG. 1.

In a preferred embodiment the method further includes printing a carbon layer on the substrate prior to the first step above and further printing a carbon layer over the second layer of the color. The carbon layer includes a conductive carbon powder.

At any stage electrical connections may be printed in contact with the positive and negative pole.

While the invention has been described with respect to a limited number of embodiments, it will be appreciated that many variations, modifications and other applications of the invention may be made.

What is claimed is:

1. An application comprising an electrically operated device and a flexible thin layer open liquid state electrochemical cell for providing said device with electrical power for its operation, said electrochemical cell including a first layer of insoluble negative pole, a second layer of insoluble positive pole and a third layer of aqueous electrolyte, said third layer being disposed between said first and second layers and including:
    (a) a deliquescent material for keeping the open cell wet at all times;
    (b) an electroactive soluble material for obtaining required ionic conductivity; and
    (c) a watersoluble polymer for obtaining a required viscosity for adhering said first and second layers to said third layer.

2. The application of claim 1, wherein said device includes a substrate material and at least one electronic component attached to said substrate material, said at least one electronic component is for performing a sensible performance.

3. The application of claim 2, wherein said substrate is selected from the group consisting of a greeting card, a business card, a package of a food product and a printed matter.

4. The application of claim 2, wherein said sensible performance is audial or visual.

5. The application of claim 4, wherein said audial performance is selected from the group consisting of a melody, words of a language and telephone dial tones.

6. The application of claim 2, wherein said device includes a power switch.

7. The application of claim 2, wherein said at least one electronic component is selected from the group consisting of an audio device and a light emitting device.

8. The application of claim 7, wherein said audio device includes an audio chip and an echo chamber.

9. The application of claim 7, wherein said light emitting device is a low-current led.

10. The application of claim 1, wherein said device is a timer.

11. The application of claim 10, wherein said timer includes a substrate material and a timer chip attached to said substrate material, said timer chip is presetable for timing a time period and for prompting a sensible performance when said time period has elapsed.

12. The application of claim 11, wherein said performance is by an audio or light emitting device.

13. The application of claim 11, wherein said sensible performance is audial or visual.

14. The application of claim 13, wherein said audial performance is selected from the group consisting of a melody, words of a language and an alarm.

15. The application of claim 11, wherein said timer chip is programmable.

16. The application of claim 11, wherein said timer chip is resetable.

17. The application of claim 12, wherein said audio device includes an audio chip and an echo chamber.

18. The application of claim 12, wherein said light emitting device is a low-current led.

19. The application of claim 11, wherein said timer is a drug timer.

20. The application of claim 1, wherein said device is an active pad for transdermal delivery of a compound.

21. The application of claim 20, wherein for said transdermal delivery of said compound said active pad employs a strategy selected from the group consisting of iontophoresis, ultrasound and electroporation.

22. The application of claim 20, wherein said compound is selected from the group consisting of a pharmaceutical compound, a cosmetic compound and an anesthetic compound.

23. The application of claim 1, wherein said device is an active pad for transdermal recovery of a compound from a body.

24. The application of claim 1, wherein said device is a thermometer.

25. The application of claim 24, wherein said thermometer includes a thermistor sensor and an electronic chip, said sensor is for sensing a heat magnitude and converting said heat magnitude into electrical parameter of a magnitude corresponding to said heat, said chip is for quantifying said parameter and for translating said parameter into an output of a temperature value.

26. The application of claim 25, wherein said thermometer further includes a display for displaying said temperature value.

27. The application of claim 1, wherein said device is a glucose sensor.

28. The application of claim 27, wherein said glucose sensor includes a needle for rupturing the skin and obtaining a blood sample, a glucose oxidaze based glucose sensor, a potenciostat and an electronic chip for quantifying a glucose level in said blood sample.

29. The application of claim 1, wherein said device is a game.

30. The application of claim 29, wherein said game includes distributed un-raveled components, said un-raveled components become revealed if current from said cell arrives simultaneously or in a predetermined order to said components, said arrival of current is activated by a player.

* * * * *